US00PP14842P3

(12) United States Plant Patent

Hasegawa

(10) Patent No.: US PP14,842 P3
(45) Date of Patent: Jun. 1, 2004

(54) CARNATION PLANT NAMED 'CFPC MANGO'

(50) Latin Name: *Dianthus caryophyllus*
Varietal Denomination: CFPC Mango

(75) Inventor: Oscar T. Hasegawa, Salinas, CA (US)

(73) Assignee: California Florida Plant Company, L.P., Salinas, CA (US)

( * ) Notice: Subject to any disclaimer, the term of this patent is extended or adjusted under 35 U.S.C. 154(b) by 0 days.

(21) Appl. No.: 10/208,143

(22) Filed: Jul. 29, 2002

(65) Prior Publication Data

US 2004/0019942 P1 Jan. 29, 2004

(51) Int. Cl.[7] ..... A01H 5/00
(52) U.S. Cl. ..... Plt./273
(58) Field of Search ..... Plt./273

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of carnation plant producing attractive orange flowers.

1 Drawing Sheet

Classification: The present invention relates to a new Hybrid *Dianthus caryophyllus* plant.

Variety denomination: The new plant has the varietal denomination 'CFPC Mango'.

BACKGROUND OF THE INVENTION

The present invention relates to a new and distinct variety of carnation plant which was originated by crossing two undistributed, unpatented seedlings as its male and female parents. The varietal denomination of the new variety is 'CFPC Mango'.

SUMMARY OF THE INVENTION

Among the novel characteristics possessed by the new variety which distinguish it from other varieties of which I am aware are its attractive orange flowers which retain color without fading. When grown in a greenhouse in Salinas, Calif., in 4½ inch plastic pots, pinched plants are about 7 inches tall and about 7 inches in diameter. Flower diameter averages about 1¾ inches. Foliage is about 3½ inches long and about ⅞ inch wide at its widest point.

Asexual reproduction by propagation by cuttings of the new variety as performed in Salinas, Calif., shows that the foregoing and other distinguishing characteristics come true to form and are established and transmitted through succeeding propagation.

COMPARISON WITH PARENTS

The new variety differs from its parents in flower color.

BRIEF DESCRIPTION OF ILLUSTRATION

The accompanying illustration shows a typical specimen of the vegetative growth and flowers of the new variety depicted in color as nearly true as it is reasonably possible to make the same in color illustration of this character.

DESCRIPTION OF THE NEW VARIETY

The following is a detailed description of the new variety, with color terminology in accordance with The Royal Horticultural Society Colour Chart (R.H.S.C.C.). The terminology used in color description herein refers to plate numbers in the aforementioned color chart. Phenotypical expression may vary depending upon varying environmental, seasonal and cultural conditions.

The information provided herein is based on observations of 110-day-old plants grown inside commercial greenhouses at Salinas, Calif. The height of plant and flower and foliage size are established as an average using standard commercial cultural practices.

Classification:
- *Botanical.*—Hybrid *Dianthus caryophyllus.*
- *Commercial.*—Carnation, standard disbud, type, suitable for production as a pot spray.

Plant:
- *Height.*—About 7 inches.
- *Form.*—Herbaceous.
- *Growing habit.*—Semi-upright.
- *Blooming habit.*—As a spray (pot).
- *Blooming season.*—Year round.
- *Rooting time/habit.*—About 18 days.
- *Breaking action.*—Averages about 15 breaks per plant.
- *Mutation prone.*—No.
- *Disease resistance.*—Good, resistence to soil-borne diseases such as *Fusarium oxysporum,* and *F. graminearum* and root-rots such as damping off, water molds and the like as is typical of carnations.
- *Temperature tolerance.*—Wide range.

Foliage (base of plant):
- *Color.*—Upper side: Near 136B. Lower side: Near 137A.
- *Size.*—About 3½ inches long and about ⅞ inch wide.
- *Leaf base and apex.*—Leaf base edge smooth, color near 138D; leaf apex edge smooth, color near 136B.
- *Quantity.*—Numerous.
- *Shape.*—Lanceolate.
- *Texture.*—Smooth.
- *Ribs.*—Central keel.
- *Arrangement.*—Bi-lateral along stem.
- *Stem.*—Color: Near 145B. Size: Stem diameter about 3/16 inch.

*Bud.*—Shape: Ovoid. Color: Near 143C. Length: About ¾ inch. Diameter: About 7/16 inch.

*Calyx.*—Sepals: About 5. Length: About ¼ inch. Width: About ¼ inch. Color Outside: Near 143C. Inside: Near 138C.

Bloom:

*Shape.*—Rounded.

*Size.*—Diameter: About 1¾ inches. Depth: About ⅞ inch.

*Borne.*—As a spray.

*Color.*—General tonality: Orange with yellow and red markings. Upper side: Near 28C with occasional marks near 45B. Lower side: Near 29C. Center: Near 28C. Outer petals: Near 28C.

*Permanence.*—Dry up on receptacle.

*Keeping quality.*—Very good, about 3 weeks.

*Fragrance.*—Slight to none.

Petalage:

*Quantity.*—Average between 32 to 33.

*Outer petal size.*—Length: About 1½ inches. Width: About ¾ inch.

*Central petal size.*—Length: About 1¼ inches. Width: About ¾ inch.

*Texture.*—Smooth.

*Appearance.*—Shiny, petal edge finely serrated, color near 45B in continuous very fine picotee pattern less than 1/32 inch width with occasional spots near 45B and fine radial lines on a background of 28C, no yellow markings.

*Form.*—Fan shaped.

Reproductive organs:

*Stamen.*—None.

*Anthers.*—None.

*Filaments.*—None.

*Pistil.*—4. Length: About ⅞ inch. Color: Whiter than 155D.

*Stigma.*—4. Color: Whiter than 155D.

*Fertility.*—Male: Sterile. Female: Good.

*Ovary.*—Shape: Conical. Color Base: Near 155D. Body: Near 144B. Apex: Near 144B.

*Fruit.*—No fruit or seed produced.

I claim:

1. A new and distinct carnation plant of the variety substantially as herein shown and described.

* * * * *

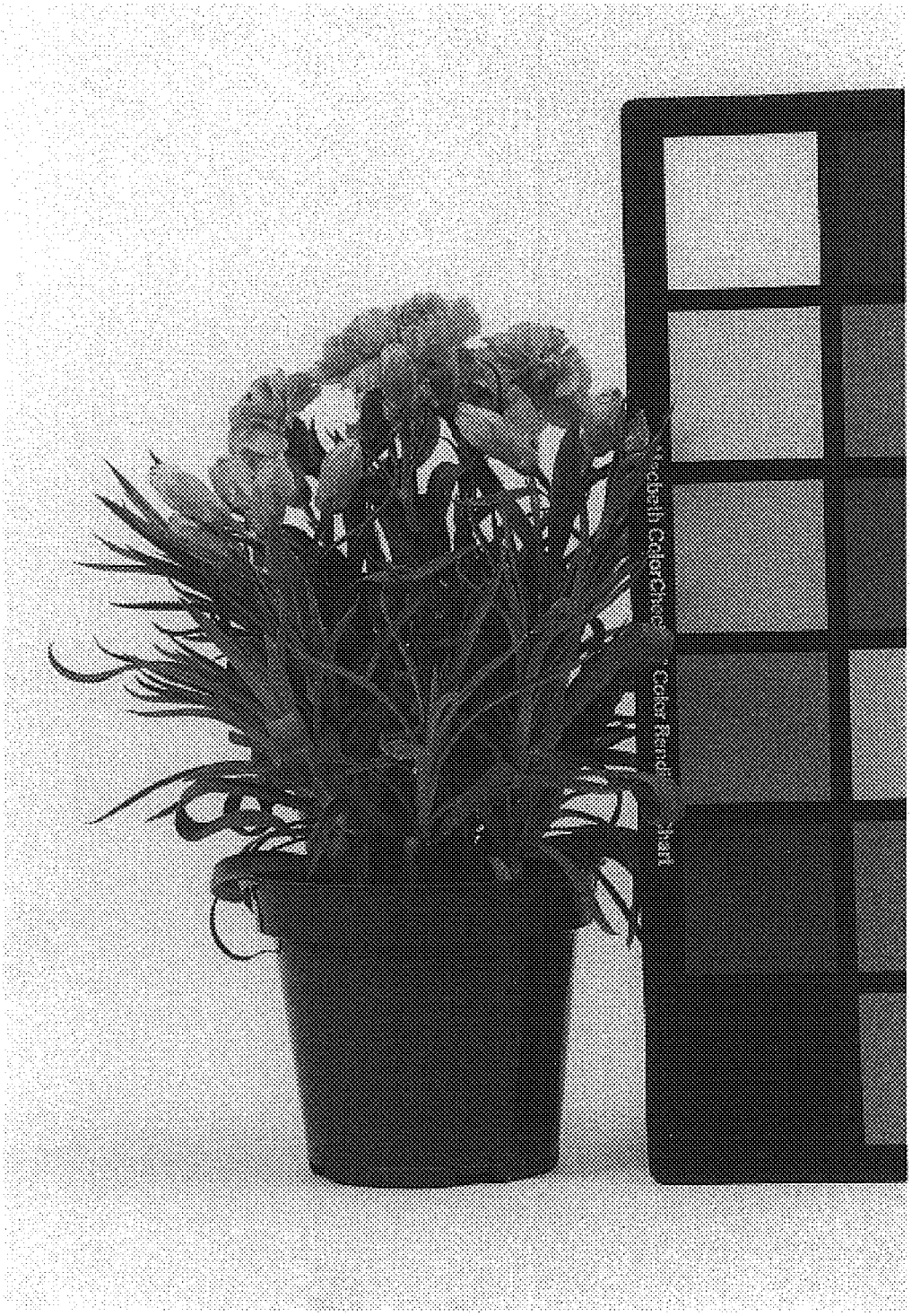
Munsell ColorChart
Color Reference
Chart